(12) United States Patent
Sato

(10) Patent No.: US 8,349,418 B2
(45) Date of Patent: Jan. 8, 2013

(54) PLANT-DERIVED NATURAL BIODEGRADABLE MATERIAL

(75) Inventor: Seiko Sato, Tokyo (JP)

(73) Assignee: Seiko Sato, Tokyo (JP)

( * ) Notice: Subject to any disclaimer, the term of this patent is extended or adjusted under 35 U.S.C. 154(b) by 686 days.

(21) Appl. No.: 12/516,442

(22) PCT Filed: Nov. 26, 2007

(86) PCT No.: PCT/JP2007/001303
§ 371 (c)(1),
(2), (4) Date: Jun. 16, 2009

(87) PCT Pub. No.: WO2008/065749
PCT Pub. Date: Jun. 5, 2008

(65) Prior Publication Data
US 2010/0086714 A1   Apr. 8, 2010

(30) Foreign Application Priority Data

Nov. 30, 2006 (JP) .................... 2006-324458

(51) Int. Cl.
*B32B 1/02* (2006.01)
(52) U.S. Cl. .................. 428/35.7; 435/118; 549/510
(58) Field of Classification Search .......... 428/35.5; 435/118; 549/510
See application file for complete search history.

(56) References Cited

U.S. PATENT DOCUMENTS 5,801,025 A   9/1998 Ohara et al.
2006/0111511 A1   5/2006 Narayan et al.

FOREIGN PATENT DOCUMENTS

| JP | 04-335060 | 11/1992 |
| JP | 05-093049 | 4/1993 |
| JP | 06-340753 | 12/1994 |
| JP | 07-102114 | 4/1995 |
| JP | 07-265065 | 10/1995 |

(Continued)

OTHER PUBLICATIONS

Aslim et al., "Determination of PHB Growth Quantities of Certain *Bacillus* Species Isolated from Soil," Turkish Electronic Journal of Biotechnology, 2002, pp. 24-30.

(Continued)

*Primary Examiner* — D. Lawrence Tarazano
*Assistant Examiner* — Hamid R Badr
(74) *Attorney, Agent, or Firm* — Kenneth H. Sonnenfeld; Margaret B. Brivanlou; King & Spalding

(57) ABSTRACT

It is intended to provide a natural biodegradable material having both properties of biodegradability and mechanical strength; a biodegradable film or container produced from the natural biodegradable material; a binder for producing the biodegradable material; and a method for producing these. A natural polymeric substance which has a cellulose-like property of having hydroxy group which is not present in a petroleum-derived polymeric compound, and which moreover has a polypropylene-like structure is obtained by the steps of using a cereal starch such as Kaoliang starch as a culture raw material, adding a microorganism belonging to the genus *Bacillus* to the raw material to conduct a culture, and recovering a viscous polymeric substance. A biodegradable material having biodegradability comparable to that of cellulose and also having a mechanical strength property of polypropylene can be obtained by using the natural polymeric substance as a binder and mixing starch and/or shell powder thereto. A film or container produced by using this biodegradable material has superior properties in both biodegradability and mechanical strength.

4 Claims, 1 Drawing Sheet

FOREIGN PATENT DOCUMENTS

| | | |
|---|---|---|
| JP | 07-285108 | 10/1995 |
| JP | 09-121877 | 5/1997 |
| JP | 2000-072961 | 3/2000 |
| JP | 2000-229312 | 8/2000 |
| JP | 2000-229661 | 8/2000 |
| JP | 2000-327839 | 11/2000 |
| JP | 2000-355008 | 12/2000 |
| JP | 2001-049098 | 2/2001 |
| JP | 2001-079816 | 3/2001 |
| JP | 2002-097301 | 4/2002 |
| JP | 2002-167470 | 6/2002 |
| JP | 2002-249981 | 9/2002 |
| JP | 2004-299711 | 10/2004 |
| JP | 2005-133224 | 5/2005 |
| JP | 2006-042699 | 2/2006 |
| JP | 2006-122317 | 5/2006 |
| WO | WO 2006/055505 | 5/2006 |

OTHER PUBLICATIONS

Xu et al., "Efficient Production of Poly($\gamma$-glutamic acid) by Newly Isolated *Bacillus subtilis* NX-2," Process Biochemistry, 2005, pp. 519-523.

Hong et al., "A Rapid Method for Detecting Bacterial Polyhydroxyalkanoates in Intact Cells by Fourier Transform Infrared Spectroscopy," Appl. Microbiol. Biotechnol., 51, pp. 523-526, 1999.

Gouda et al., "Production of PHB by a *Bacillus megaterium* Strain Using Surgercane Molasses and Corn Steep Liquor as Sole Carbon and Nitrogen Sources," Microbiol. Res., 156, pp. 201-207, 2001.

[Figure 1]
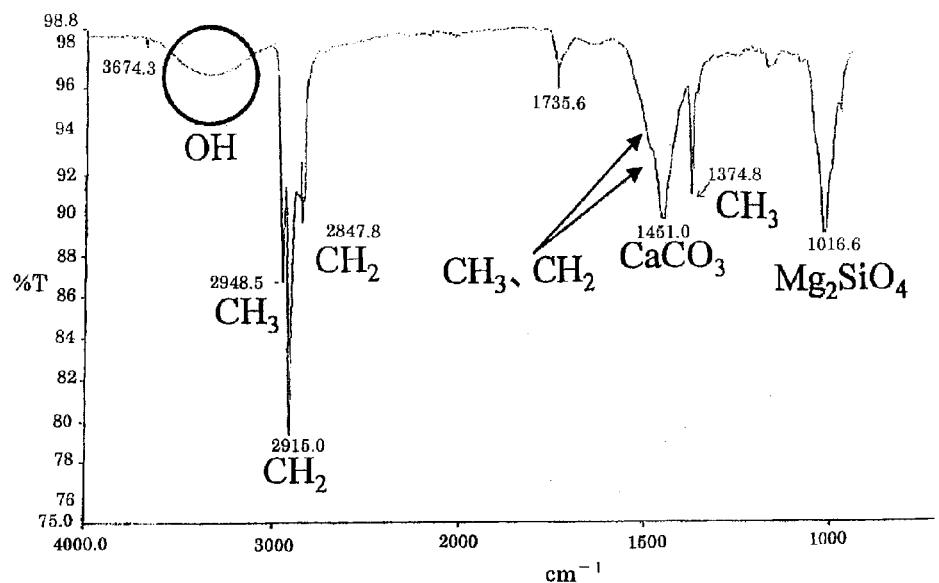
[Figure 2]
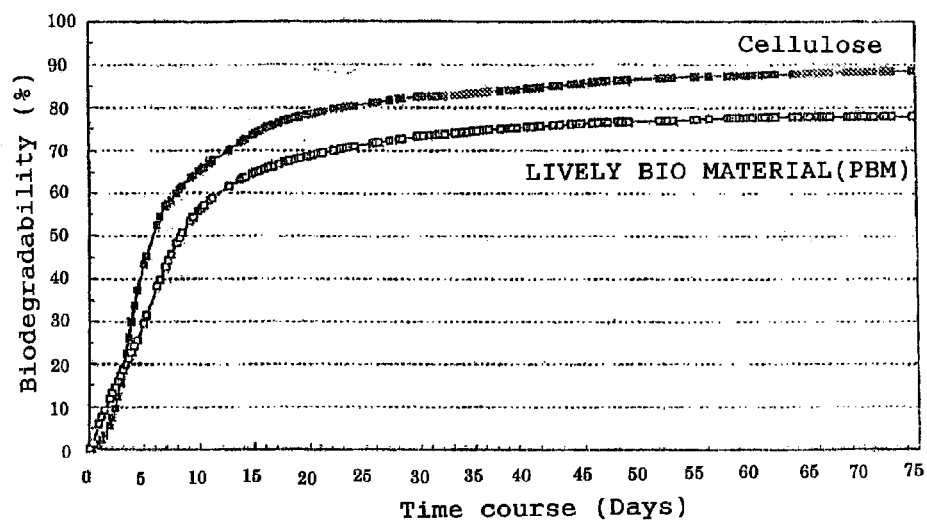

PLANT-DERIVED NATURAL BIODEGRADABLE MATERIAL

TECHNICAL FIELD

The present invention consists of a natural polymeric substance which is plant-derived and has a property of polypropylene; a natural biodegradable material which is produced by using the natural polymeric substance, which has a cellulose-like biodegradation curve and a property of polypropylene, and which is used for production of a biodegradable film or container having properties of both biodegradability and mechanical strength; a binder used for production of a biodegradable material containing the natural polymeric substance as a main component; a biodegradable film or container produced from the natural biodegradable material; and a method for producing these.

BACKGROUND ART

Plastic products have recently been used for packaging and containers for foods, cosmetics or pharmaceutical products; for horticultural goods such as pots; or for agricultural materials. Used plastic products are either burned or directly dumped as a waste. When the wastes are burned, however, it requires a huge cost and raises environmental problems such as exhaust gas. On the other hand, when the wastes are directly dumped, it also raises an environmental problem of piled-up junks, since those wastes are resistant to degradation in nature. Therefore, biodegradable plastic materials that are easily degraded in nature have been studied and developed in recent years.

Various biodegradable plastic materials are disclosed including a plastic material in which a biodegradable plant material or the like is bound by using a biodegradable binder, a plastic material in which a synthesized biodegradable plastic is used, and a plastic material in which a microorganism or a biodegradable polymeric material yielded by a microorganism is used. With regard to products using a biodegradable plant material, etc., containers made of a biodegradable material is disclosed in, for example, Japanese Laid-Open Patent Application Nos. 2000-229312, 2000-355008, 2001-79816, and 2002-249981, wherein the raw material plant powder containing rice husk as a main component is compressedly molded by hot-pressing by using a binder consisting of a biodegradable substance such as starch, rosin, dammar, copal, gelatin and shellack. Further, Japanese Laid-Open Patent Application No. 2000-229661 describes that a biodegradable container such as a tray, plate, pack and cup is produced from leaves, stems, husks, skins, etc. of reed, straw, corn, bamboo, kaoliang, kenaf, palm and the like by using an edible paste such as a gelatin paste as an adhesive for bonding.

Japanese Laid-Open Patent Application No. 2000-327839 discloses production of a container made of a biodegradable material, wherein the raw material plant powder such as rice husk is mixed with such as bran of cereals like rice bran and molded. Japanese Laid-Open Patent Application No. 2002-23262 discloses a biodegradable plastic, wherein a natural material such as sugarcane, pineapple and seaweeds is refined and used as a main material, which main material is mixed with plant fiber such as corn, pulse, potatoes, old rice, coarse cereal and weed, and the mixture is then molded into the biodegradable plastic by using a binder consisting of a natural material such as persimmon tannin, yam paste powder, pine resin and lacquer. Japanese Laid-Open Patent Application No. 2006-122317 discloses production of a biodegradable sheet, wherein fiber of waste papers is bound by starch paste or yeast slop, or by a biodegradable binder such as polyester resin, polylactide resin, natural rubber resin, and polyvinylalcohol.

Further, Japanese Laid-Open Patent Application No. 7-102114 discloses a biodegradable cellulose ester composition wherein cellulose ester such as cellulose diacetate and cellulose triacetate is mixed with starches and a plasticizer. As for products using a synthetic biodegradable plastic, Japanese Laid-Open Patent Application Nos. 4-335060, 6-340753, 2000-72961, 2001-49098 and 2004-299711 disclose biodegradable resin compositions and compacts using polylactate, copolymer of polylactate, and resin mixture of polylactate.

As for products using a microorganism or a biodegradable polymeric material yielded by a microorganism, products using yeast cells are disclosed, for example, in the following: Japanese Laid-Open Patent Application No. 2002-97301 discloses a biodegradable resin composition consisting of yeast which has been resinified by heating and pressurization; Japanese Laid-Open Patent Application No. 2002-167470 discloses a biodegradable plastic wherein yeast is mixed with a biodegradable plastic such as a resin yielded by a microorganism such as polyhydroxybutyrate, a chemically synthesized resin such as polycaprolactone, polybutylenesuccinate, polyethylenesuccinate, polyglycolic acid, polylactate and polyvinylalcohol, or a denatured resin in which a natural substance such as acetylcellulose and thermoplastic starch are denatured; and Japanese Laid-Open Patent Application No. 7-285108 discloses a wood biodegradable material wherein fiber, which has been dry-fibrillated from waste papers, is mixed with yeast bran followed by pressurization and heating.

Further, as examples of the products using a biodegradable polymeric material yielded by microorganisms, Japanese Laid-Open Patent Application No. 2005-133224 discloses a biodegradable resin molding material to be used as a molding material for such as food containers, wherein pulp fiber such as delignified rice straw, wheat straw, sugarcane chaff (Bargasse), kenaf and Ipil-ipil; β-1,3-D-glucoside polysaccharides yielded by Alcaligenes faecalis, or saccharides such as maltotriose polysaccharides yielded by black yeast (Aureobasidium pullulans) (for improvement of gas barrier property); and a silk fibroin spun by silkworms, or a protein-like substance spun by spiders (for reducing moisture permeability) are mixed. Japanese Laid-Open Patent Application No. 2006-142699 discloses a biodegradable plastic produced by the steps comprising: producing L-lactate by filamentous bacterium *Amylomyces rouxii* from a raw material containing sucrose such as sugarbeet and sugarcane extracts; and either producing polylactate by dehydrating and condensing the L-lactate, or producing polylactate by first synthesizing cyclic lactide (dimer) from the L-lactate, which cyclic lactide is then subjected to purification followed by ring-opening polymerization.

As for a biodegradable polymeric material yielded by microorganisms, polyester of poly-3-hydroxybutyrate which is a homopolymer of 3-hydroxybutyrate and is yielded by *Bacillus megaterium* has long been known (M. Lemoigne, Ann. Inst. Pasteur, 39, 144, 1925). For the purpose of improving hard and brittle properties of the poly-3-hydroxybutyrate, Japanese Laid-Open Patent Application Nos. 5-93049 and 7-265065 disclose production of a copolymeric polyester of 3-hydroxybutyrate and 3-hydroxyhexanoate from a fatty acid such as oleic acid or fat such as olive oil by employing a fermentation method using *Aeromonas caviae*, and disclose use of the copolymeric polyester as a biodegradable material.

As shown above, there has been conducted various studies concerning development of biodegradable polymeric materials, and production methods of biodegradable polymeric materials employing various methods by using various raw materials are disclosed. Conventionally, however, biodegradable polymeric materials having sufficient properties as a polymeric material enough to meet the practical requirements in view of both easy degradability and mechanical strength necessary for use as a film, container, etc., have not been developed. Therefore, such biodegradable materials are currently not practiced sufficiently.

Patent Reference 1: Japanese Laid-Open Patent Application No. 4-335060
Patent Reference 2: Japanese Laid-Open Patent Application No. 5-93049
Patent Reference 3: Japanese Laid-Open Patent Application No. 6-340753
Patent Reference 4: Japanese Laid-Open Patent Application No. 7-102114
Patent Reference 5: Japanese Laid-Open Patent Application No. 7-265065
Patent Reference 6: Japanese Laid-Open Patent Application No. 7-285108
Patent Reference 7: Japanese Laid-Open Patent Application No. 2000-72961
Patent Reference 8: Japanese Laid-Open Patent Application No. 2000-229312
Patent Reference 9: Japanese Laid-Open Patent Application No. 2000-229661
Patent Reference 10: Japanese Laid-Open Patent Application No. 2000-327839
Patent Reference 11: Japanese Laid-Open Patent Application No. 2000-355008
Patent Reference 12: Japanese Laid-Open Patent Application No. 2001-49098
Patent Reference 13: Japanese Laid-Open Patent Application No. 2001-79816
Patent Reference 14: Japanese Laid-Open Patent Application No. 2002-23262
Patent Reference 15: Japanese Laid-Open Patent Application No. 2002-97301
Patent Reference 16: Japanese Laid-Open Patent Application No. 2002-167470
Patent Reference 17: Japanese Laid-Open Patent Application No. 2002-249981
Patent Reference 18: Japanese Laid-Open Patent Application No. 2004-299711
Patent Reference 19: Japanese Laid-Open Patent Application No. 2005-133224
Patent Reference 20: Japanese Laid-Open Patent Application No. 2006-142699
Patent Reference 21: Japanese Laid-Open Patent Application No. 2006-122317
Non-patent Reference 1: M. Lemoigne, Ann. Inst. Pasteur, 39, 144, 1925

DISCLOSURE OF THE INVENTION

Object to be Solved by the Invention

The object of the present invention is to provide a natural biodegradable material having properties of both biodegradability and mechanical strength, thus having superior properties from the practical point of view; a biodegradable film or container produced from the natural biodegradable material; a binder for producing the biodegradable material; and a method for producing these.

Means to Solve the Object

In the course of the keen study on production of a biodegradable material from a natural substance in order to solve the problems mentioned above, the present inventor has found that a natural polymeric substance which has a cellulose-like property of having hydroxy group that is not present in a petroleum-derived polymeric compound and which has a polypropylene-like structure can be obtained by the steps comprising: using a cereal starch such as Kaoliang starch as a culture raw material; adding a microorganism belonging to the genus *Bacillus* to the raw material to conduct a culture; and recovering a viscous polymeric substance. The present inventor has further found that a biodegradable material having biodegradability comparable to that of cellulose and also having a mechanical strength property of polypropylene can be obtained by using thus obtained natural polymeric substance as a binder and admixing starch and/or shell powder with the binder. The present invention was thus completed.

A biodegradable film or container having a superior biodegradability, mechanical strength, and other practically desirable properties can be produced by using a biodegradable material of the present invention. Examples of the microorganism belonging to the genus *Bacillus* to be used in the present invention include *Bacillus subtilis*, *Bacillus pumilus* and *Bacillus thuringiensis*. It is preferred to use a microorganism mixture consisting of at least 2 types of microorganisms selected from these exemplified microorganisms. It is particularly preferred to use a microorganism mixture consisting of 3 types of microorganisms selected from *Bacillus subtilis*, *Bacillus pumilus* and *Bacillus thuringiensis*.

In the present invention, it is desirable to promote bacterial proliferation and to induce spore formation in the fermentation step, and it is preferred to add silicate or magnesium silicate in order to promote bacterial proliferation and spore formation. A natural polymeric substance produced by a production method of the present invention shows absorption spectrum of a hydroxy group and polypropylene group by infrared absorption spectrum analysis (IR) (FIG. 1), and its structure is represented by the constitutional unit molecular formula of $(C_{11}H_{16}O_7)$, and it is presumed to be a compound represented by formula (I).

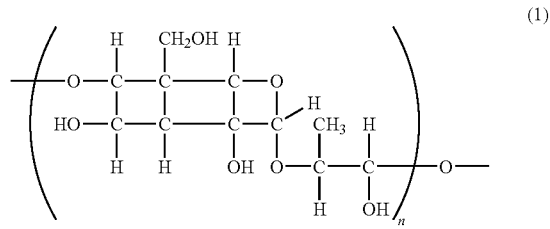

In the formula, n represents a positive integer.

The present invention encompasses an embodiment wherein a natural polymeric substance produced by a production method of the present invention is used as a binder for production of a natural biodegradable material. Further, a natural biodegradable material for production of a natural biodegradable film or container can be produced by mixing the binder with starch and/or shell powder, followed by molding. The present invention enables production of a biodegradable film or container consisting of a natural material by carrying out molding by using the natural biodegradable material. When producing a biodegradable film in the present invention, it is preferred to mix starch at 5-10 wt %, shell powder at 5-10 wt % and a binder of the present invention at 80-90 wt %, relative to the total weight of the biodegradable material and then carrying out molding. When producing a biodegradable container, it is preferred to mix starch at 50-60 wt %, shell powder at 10-20 wt % and the binder according to (7) below at 30-40 wt %, relative to the total weight of the biodegradable material and then carrying out molding.

Specifically, the present invention relates to: (1) a method for producing a natural polymeric substance for molding a biodegradable material, the method comprising: using a cereal starch as a culture raw material; adding a microorganism belonging to the genus *Bacillus* to the raw material and conducting a culture, and recovering a viscous polymeric substance that shows absorption spectrum of hydroxy group and polypropylene group by infrared absorption spectrum analysis (IR); (2) the method for producing a natural polymeric substance for molding a biodegradable material according to (1), wherein the cereal starch culture raw material is Kaoliang starch; (3) the method for producing a natural polymeric substance according to (1), wherein the microorganism belonging to the genus *Bacillus* is a microorganism mixture of at least 2 types selected from *Bacillus subtilis*, *Bacillus pumilus* and *Bacillus thuringiensis*; (4) the method for producing a natural polymeric substance according to (3), wherein the microorganism belonging to the genus *Bacillus* is a microorganism mixture of 3 types selected from *Bacillus subtilis*, *Bacillus pumilus* and *Bacillus thuringiensis*; and (5) the method for producing a natural polymeric substance according to (1), wherein silicate or magnesium silicate is added in a step of culturing the microorganism belonging to the genus *Bacillus*.

The present invention further relates to: (6) a natural polymeric substance produced by the method for producing a natural polymeric substance according to any one of (1) to (4), wherein the natural polymeric substance shows absorption spectrum of hydroxy group and polypropylene group by infrared absorption spectrum analysis (IR); (7) the natural polymeric substance according to (6), wherein structure of the natural polymeric substance has a presumed structural formula of a compound whose constitutional unit molecular formula is represented by $(C_{11}H_{16}O_7)$, and which is shown by formula (1)

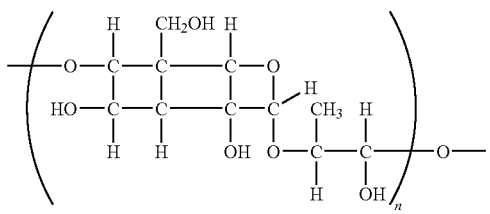

(1)

(wherein n represents a positive integer); (8) a binder for producing a natural biodegradable material having the natural polymeric substance according to (6) or (7) as a main component; (9) a natural biodegradable material for producing a natural biodegradable film or container, wherein the binder according to (8) is mixed with starch and/or shell powder and molded; and (10) the natural biodegradable material for producing a natural biodegradable film or container according to (9), wherein the starch is a chemically denatured starch.

The present invention still further relates to: (11) the natural biodegradable material for producing a natural biodegradable film or container according to (9) or (10), wherein the shell powder is mixed with the binder according to (8) to mold a pellet; (12) a biodegradable film or container consisting of a natural material, wherein starch and shell powder are mixed with the binder according to (8) and molded; (13) a biodegradable film consisting of the natural material according to (12), wherein starch at 5-10 wt %, shell powder at 5-10 wt %, and the binder according to (8) at 80-90 wt %, relative to the total weight of the biodegradable material, are mixed and molded; and (14) a biodegradable container consisting of the natural material according to (12), wherein starch at 50-60 wt %, shell powder at 10-20 wt %, and the binder according to (8) at 30-40 wt %, relative to the total weight of the biodegradable material, are mixed and molded.

BRIEF EXPLANATION OF THE DRAWINGS

FIG. 1 is a drawing showing the absorption spectrum as analyzed by infrared absorption spectrum analysis (IR analysis) of a natural polymeric substance produced according to the present invention.

FIG. 2 is a drawing showing the result of the biodegradation test conducted in accordance with ISO 14855 by NSF International (U.S.A.) for a natural biodegradable material produced by the present invention.

BEST MODE OF CARRYING OUT THE INVENTION

The present invention comprises a method for producing a natural polymeric substance for use in molding a biodegradable material, which method comprises adding a microorganism belonging to the genus *Bacillus* to a cereal starch such as Kaoliang starch as a culture raw material, culturing thereof, and recovering a viscous polymeric substance. The natural polymeric substance as a binder is mixed with starch and/or shell powder, which mixture is then molded to prepare a natural biodegradable material. Thus obtained natural biodegradable material is molded to produce a biodegradable film or container consisting of a natural material.
(Culture Raw Material)

In the present invention, a cereal starch may be used as a culture raw material. Examples of the cereal starch include Kaoliang; corn; wheats such as rice, barley, oat, and rye; Job's tears; pulse; Japanese barnyard millet; and millet. Among these, Kaoliang starch is particularly superior as a culture raw material for producing a viscous polymeric substance of the present invention. When using Kaoliang starch as a culture raw material in the present invention, a corn starch, potato starch and other starches may be appropriately compounded to the Kaoliang starch.
(Microorganism to be Used)

In the present invention, a microorganism belonging to the genus *Bacillus* is used as a microorganism for production of a natural polymeric substance by using Kaoliang starch as a culture raw material. As for the microorganism, it is preferred to use a microorganism mixture consisting of at least 2 types of microorganisms selected from *Bacillus subtilis*, *Bacillus pumilus* and *Bacillus thuringiensis*. It is particularly preferred to use a microorganism mixture of 3 types of microorganisms selected from *Bacillus subtilis*, *Bacillus pumilus* and *Bacillus thuringiensis*. Properties of the natural polymeric substance to be produced can be adjusted by appropriately adjusting the mixing ratio of a microorganism mixture consisting of the 3 types of microorganisms. These microorganisms belonging to the genus *Bacillus* have been conventionally used as a microorganism for compost and in degradation treatment of sludge, etc. (Japanese Laid-Open Patent Application Nos. 2003-190993, 2003-342092 and 2004-65190), and can be easily obtained by a third party.

(Production of a Natural Polymeric Substance)

According to the present invention, a natural polymeric substance is produced by using Kaoliang starch as a culture raw material, adding a microorganism belonging to the genus *Bacillus* to the raw material and culturing thereof, and then recovering a viscous polymeric substance. Basically, usual conditions for culturing microorganisms belonging to the genus *Bacillus* can be employed as conditions for the culture. The present invention is intended to produce and recover a natural polymeric substance by culturing a microorganism belonging to the genus *Bacillus*, and it is preferred to conduct the culture under the conditions promoting spore formation, since production of a natural polymeric substance by the microorganism belonging to the genus *Bacillus* is enhanced at the spore formation stage during the microorganism is cultured. Such conditions include adding silicate or magnesium silicate (fossil powder of coral, or shell) to the culture solution in the culture step. Silicate is necessary for spore formation of microorganisms and magnesium promotes proliferation speed of microorganisms. Therefore, spore formation can be promoted by adding these components.

(Natural Polymeric Substance)

A natural polymeric substance produced by a production method of the present invention demonstrates the absorption spectrum shown in FIG. 1 as analyzed by infrared absorption spectrum analysis (IR). This absorption spectrum suggests absorption caused by the presence of cellulose-like hydroxy group that are not comprised in a petroleum-derived synthesized polymeric substance. Absorption indicating the presence of polypropylene group is also suggested. In view of these properties, a natural polymeric substance produced by the present invention has biodegradability comparable to cellulose, and a natural biodegradable material produced by using the natural polymeric substance can be provided with air permeability similar to that of cellulose. A natural polymeric substance obtained by the present invention can be used as a binder for producing a natural biodegradable material which contains the substance as a main component. Structure of a natural polymeric substance of the present invention is represented by the constitutional unit molecular formula of $(C_{11}H_{16}O_7)$, and it is presumed to be a compound represented by formula (1).

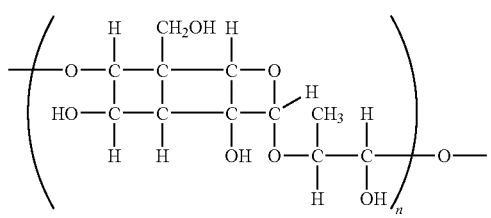

In the formula, n represents a positive integer.

(Natural Biodegradable Material)

In the present invention, starch and/or shell powder is mixed with a binder of the present invention and molded to prepare a natural biodegradable material to be used for producing a natural biodegradable film or container. Usually, it is molded in pellets, but it can either be granular or powdery. As for starch to be mixed for preparing the natural biodegradable material, corn starch, potato starch and the like may be appropriately used, but it is preferred to use a processed starch in which the above-mentioned starch has been processed (modified) so as to have a net-like molecular structure by altering the molecular structure. Examples of the processed starch include oxidized starch, esterified starch, etherified starch and cross-linked starch. Addition of shell powder, that is, addition of calcium carbonate and calcium silicate that are the main components of a shell, is effective for improving strength and texture of the molded products.

In the present invention, compounding ratio of starch, shell powder and a binder in preparation of a natural biodegradable material is as shown in Table 1.

TABLE 1

|  | Starch | Adhesive (Binder) | Shell |
| --- | --- | --- | --- |
| Containers | 50-60% | 30-40% | 10-20% |
| Films | 5-10% | 80-90% | 5-10% |

Specifically, when producing a biodegradable film, starch at 5-10 wt %, shell powder at 5-10 wt %, and a binder of the present invention at 80-90 wt %, relative to the total weight of the biodegradable material are mixed and molded. Further, when producing a biodegradable container, starch at 50-60 wt %, shell powder at 10-20 wt %, and a binder of the present invention at 30-40 wt %, relative to the total weight of the biodegradable material are mixed and molded.

(Production of a Biodegradable Film and Container)

In the present invention, a biodegradable film and container can be molded and produced by using a biodegradable material of the present invention and employing known molding means. Although it is not restricted in the present invention, a biodegradable material is preferably prepared in a pellet form. Production of pellets of the biodegradable material and a biodegradable film is characterized in that the raw material is subjected to stretch molding, because the powder of a biodegradable material is heated and pressed. Molded preparations with good physical properties can be obtained by employing said molding method. A molding method employed in the present invention is exemplified by an inflation molding method for molding films, and by a vacuum molding (molding of trays) and a vacuum pressure molding (molding of cups) for molding containers.

(Characteristics of a Biodegradable Film and Container)

The present invention provides a biodegradable film and container consisting of a natural material and having biodegradability comparable to that of cellulose as well as mechanical strength property of polypropylene. Further, since a biodegradable film and container produced in the present invention are plant-derived, it is possible to obtain products having air permeability that is lacking in petroleum-derived synthetic plastics. When a film or container of the present invention is used as a packaging or container for fruits or vegetables, it can be expected because of this air permeability that the internal ethylene gas and the like can be efficiently emitted and that the film or container are hard to be fogged up. Therefore, use of such film or container can achieve practical advantage in the distribution of commercial goods such that the best-before date of products can be extended or that antifogging treatment becomes unnecessary because of the air permeability.

The present invention is explained more specifically in the following by way of Examples, but the technical scope of the present invention shall not be restricted to these exemplifications.

EXAMPLE 1

Production of a Natural Biodegradable Material (Production of a Natural Polymeric Substance)

1 kg of Kaoliang starch was used as a culture raw material; grained fruit pulp of jujube was added as a nutrient source; 10-15 wt % of water was added; as a culture microorganism, 3 types of microorganisms consisting of *Bacillus subtilis*, *Bacillus pumilus* and *Bacillus thuringiensis* were added at about the same ratio respectively as a microorganism mixture; and the culture was carried out under the temperature condition of about 40° C. In carrying out the culture, about 100 g of magnesium silicate (shell powder) was added to accelerate the proliferation rate and to promote the spore formation. Spore was formed after 48 hours from the commencement of culture, and cell wall of the spore was covered with a viscous substance. The cultured substance of this situation was mixed and stirred in hot water of 60-98° C. or in sugar water, and it was possible to obtain a highly viscous polymeric substance with a stable physical property.

(Identification of a Natural Polymeric Substance)

Thus prepared polymeric substance was identified by infrared absorption spectrum analysis (IR analysis). The absorption spectrum is shown in FIG. 1. As shown by the absorption spectrum of the figure, the polymeric substance absorbs hydroxy group not contained in petroleum-derived synthetic plastics, and also shows absorption of alkenes such as propylene. The polymeric substance was thus identified as a novel polymeric substance having OH group as cellulose do and having a polypropylene-like structure.

(Production of a Natural Biodegradable Material)

A natural biodegradable material was produced by using the natural polymeric substance produced in the above Example as a binder. Specifically, about 100 g of shell powder was added to 1.2 kg of a mixture of corn starch and potato starch, to which about 100-200 g of a binder consisting of the above-mentioned polymeric substance was added. The mixture was heated at 115-120° C. and molded under pressurization to make pellets. Natural biodegradable material preparations for producing containers were thus produced.

(Biodegradation Test for a Natural Biodegradable Material)

Biodegradation test was conducted by using the natural biodegradable material preparations mentioned above. The biodegradation test was conducted in accordance with the ISO 14855 biodegradation test by NSF International (U.S.A.). The result is shown in FIG. 2. As shown in FIG. 2, the natural biodegradable material produced in Example of the present invention demonstrated the biodegradation rate of 77.8% after 75 days, which is only slightly different from the biodegradation rate of cellulose as a control material. The fact that there is only slight difference in the biodegradation rate between the natural biodegradable material and the control cellulose, and that slopes in the respective graph are almost the same indicates that biodegradation rate and biodegradability speed of a natural biodegradable material of the present invention and cellulose, which is a main component of plants, are almost the same. Thus, superior biodegradability of a natural biodegradable material of the present invention was proved.

EXAMPLE 2

Physical Property Test of a Preparation (Film) Prepared by Using a Natural Biodegradable Material Film was molded by using the natural biodegradable material prepared in Example 1 and employing an inflation molding method. The film is usually molded under the conditions of 120-210° C. The physical property test as follows was conducted for the film prepared at about 210° C. by biaxial stretch using the inflation molding method.

(Tensile Strength Test)

Test method: The average of 5 measurements for both longitudinal and sideway directions ware calculated according to the tensile test of JIS Z 1702 (1994 polyethylene film for packaging) 7.5, provided that the testing speed was set at 500 mm/min, and JIS K 7100 was followed for temperature and moisture of the testing laboratory, where temperature was set at 23±2° C. and moisture at 50±5%.

Result: The result is shown in Table 2. As shown in the table, film prepared by using a natural biodegradable material of the present invention demonstrated a superior tensile strength comparable to that of a polyethylene film.

TABLE 2

| Test Item | | Test Results | | | | | |
|---|---|---|---|---|---|---|---|
| | | No. 1 | No. 2 | No. 3 | No. 4 | No. 5 | Average |
| Tensile Strength (MPa) | Longitudinal | 47.4 | 52.2 | 47.9 | 45.6 | 48.5 | 48.3 |
| | Sideways | 46.4 | 35.9 | 33.1 | 41.0 | 40.0 | 39.3 |

(Air Permeability Test)

Test method: JIS K 7126 (Test method for gas permeability of plastic films and sheets: Type of test method: Method A (Differential pressure method), Testing temperature: 23±2° C.)

Result: The result is shown in Table 3. As shown in the table, film prepared by using a natural biodegradable material of the present invention has superior air permeability.

TABLE 3

| | Test Item | 1 | 2 | Average |
|---|---|---|---|---|
| Oxygen permeability | $mol/m^2 \cdot s \cdot Pa$ | $5.57 \times 10^{-12}$ | $5.50 \times 10^{-12}$ | $5.54 \times 10^{-12}$ |
| | $\{cm^3/m^2 \cdot 24\,hr \cdot atm\}$ | {1090} | {1080} | {1080} |
| Thickness | mm | 0.040 | 0.042 | — |
| Nitrogen permeability | $mol/m^2 \cdot s \cdot Pa$ | $1.15 \times 10^{-12}$ | $1.12 \times 10^{-12}$ | $1.14 \times 10^{-12}$ |
| | $\{cm^3/m^2 \cdot 24\,hr \cdot atm\}$ | {225} | {221} | {223} |
| Thickness | mm | 0.040 | 0.042 | — |
| Carbon dioxide permeability | $mol/m^2 \cdot s \cdot Pa$ | $2.02 \times 10^{-11}$ | $1.99 \times 10^{-11}$ | $2.00 \times 10^{-11}$ |
| | $\{cm^3/m^2 \cdot 24\,hr \cdot atm\}$ | {3950} | {3900} | {3920} |
| Thickness | mm | 0.040 | 0.042 | — |

(Heat-Resistance and Cold-Resistance Test)

Test method: Samples were left for 1 hour in a constant-temperature bath in which the temperature was kept at the following temperature conditions. The samples were then taken out from the bath and left for 30 min, after which the appearance change was visually observed and deformation by finger touch was determined.

Temperature conditions: 6 conditions of 130° C., 140° C., 150° C., −30° C., −40° C., and −50° C.

Result: As below, superior heat-resistance and cold-resistance were observed.

130° C.: No change or deformation was observed by both visual observation and finger touch.

140° C.: No appearance change was observed, but a slight deformation by finger touch was confirmed.

150° C.: No appearance change was observed, but deformation by finger touch was confirmed.

−30° C.: No change or deformation was observed by both visual observation and finger touch.

−40° C.: No change or deformation was observed by both visual observation and finger touch.

−50° C.: No change or deformation was observed by both visual observation and finger touch.

INDUSTRIAL APPLICABILITY

A biodegradable film or container consisting of a natural material having biodegradability comparable to that of cellulose and also having a mechanical strength property of polypropylene can be provided by using a natural biodegradable material of the present invention. The biodegradable films and containers can possess both biodegradability and mechanical strength properties that are practical properties necessary for the molded products and that have conventionally been difficult to be achieved. A wide way is thus opened to practical application of biodegradable films and containers. Further, based on its properties, a natural biodegradable material of the present invention can be provided with air permeability other than the above-mentioned properties, thus enabling provision of containers or packaging materials having superior properties especially as containers or packaging materials for foods.

The invention claimed is:

1. A method for producing a natural polymeric substance for use as a binder to produce a biodegradable material for molding, the method comprising:
   using a cereal starch as a culture raw material;
   adding a mixture of microorganisms belonging to the genus *Bacillus*, wherein the mixture is of at least 2 types of microorganism selected from *Bacillus subtilis*, *Bacillus pumilus*, and *Bacillus thuringiensis*, to the raw material and conducting a culture; and
   recovering a viscous polymeric substance that shows absorption spectrum of hydroxy group and polypropylene group by infrared absorption spectrum analysis (IR).

2. The method for producing a natural polymeric substance according to claim 1, wherein the cereal starch culture raw material is the starch from which Kaoliang is produced.

3. The method for producing a natural polymeric substance according to claim 1, wherein the mixture of microorganisms is of 3 types selected from *Bacillus subtilis*, *Bacillus pumilus*, and *Bacillus thuringiensis*.

4. The method for producing a natural polymeric substance according to claim 1, wherein silicate or magnesium silicate is added in a step of culturing the mixture of microorganism belonging to the genus *Bacillus*.

* * * * *